(12) United States Patent
Delarge et al.

(10) Patent No.: US 7,226,936 B2
(45) Date of Patent: Jun. 5, 2007

(54) PYRIDINIC SULFONAMIDE DERIVATIVES METHOD OF PRODUCTION AND USE THEREOF

(75) Inventors: Jacques Delarge, Dolembreux (BE); Bernard Pirotte, Oupeye (BE); Jean-Michel Dogne, Grivegnée (BE); Xavier de Leval, Louveigné (BE); Fabien Julemont, Verviers (BE)

(73) Assignee: University De Liege, Liege (BE)

( * ) Notice: Subject to any disclaimer, the term of this patent is extended or adjusted under 35 U.S.C. 154(b) by 447 days.

(21) Appl. No.: 10/488,553

(22) PCT Filed: Sep. 19, 2002

(86) PCT No.: PCT/EP02/10532

§ 371 (c)(1),
(2), (4) Date: Mar. 4, 2004

(87) PCT Pub. No.: WO03/029217

PCT Pub. Date: Apr. 10, 2003

(65) Prior Publication Data

US 2005/0020642 A1    Jan. 27, 2005

(30) Foreign Application Priority Data

Sep. 27, 2001   (EP)   .................................. 01203683

(51) Int. Cl.
*A61K 31/44*   (2006.01)
*C07D 213/65*   (2006.01)
*C07D 213/75*   (2006.01)

(52) U.S. Cl. ...................... 514/352; 514/349; 546/293; 546/304; 546/307; 546/312

(58) Field of Classification Search ................ 514/349, 514/352; 546/293, 304, 307, 312
See application file for complete search history.

(56) References Cited

OTHER PUBLICATIONS

Cignarella et al, Europ. Journ. of Med. Chem. vol. 31, Jan. 8, 1996, pp. 359-364, Synthesis and pharmacological evaluation of . . . .
Julemont et al, J. Med. Chem. vol. 45, Mar. 10, 2002, pp. 5182-5185, Spectral and Crystallographic Study of Pyridinic Analogues . . . .
Organic Syntheses, vol. 48, p. 80, 1963.
Todd, Organic Reactions, vol. IV, pp. 378-428, 1948, The Wolff-Kishner Reduction.
Bergstrom et al, Journ. of Biolog. Chem., vol. 238, No. 11, 1963 pp. 3555-3563, Prostaglandins and Related Factors.
Crofford et al, Arthritis Rheum, vol. 43, pp. 4-13, 2000, Basic biology and clinical application of specific cyclooxygenase-2 . . . .
de Leval et al, Prostalandis, Leukot., Essent. Fatty Acids, vol. 64, pp. 211-216, 2001, Evaluation of classical NSAIDs and . . . .

*Primary Examiner*—Patricia L. Morris
(74) *Attorney, Agent, or Firm*—Jacobson Holman PLLC

(57) ABSTRACT

New pyridinic sulfonamide derivatives represented by a general formula (I), wherein R1, represents a mono- or polyhalogenated C1–12-alkyl or a mono- or poly-halogenated C3–8-cycloalkyl group. The method of production of such derivatives and their use as active therapeutic substance in the treatment of diseases such as inflammation, arthrosis, cancer, angiogenesis and asthma are also reported.

8 Claims, 2 Drawing Sheets

Figure 1:
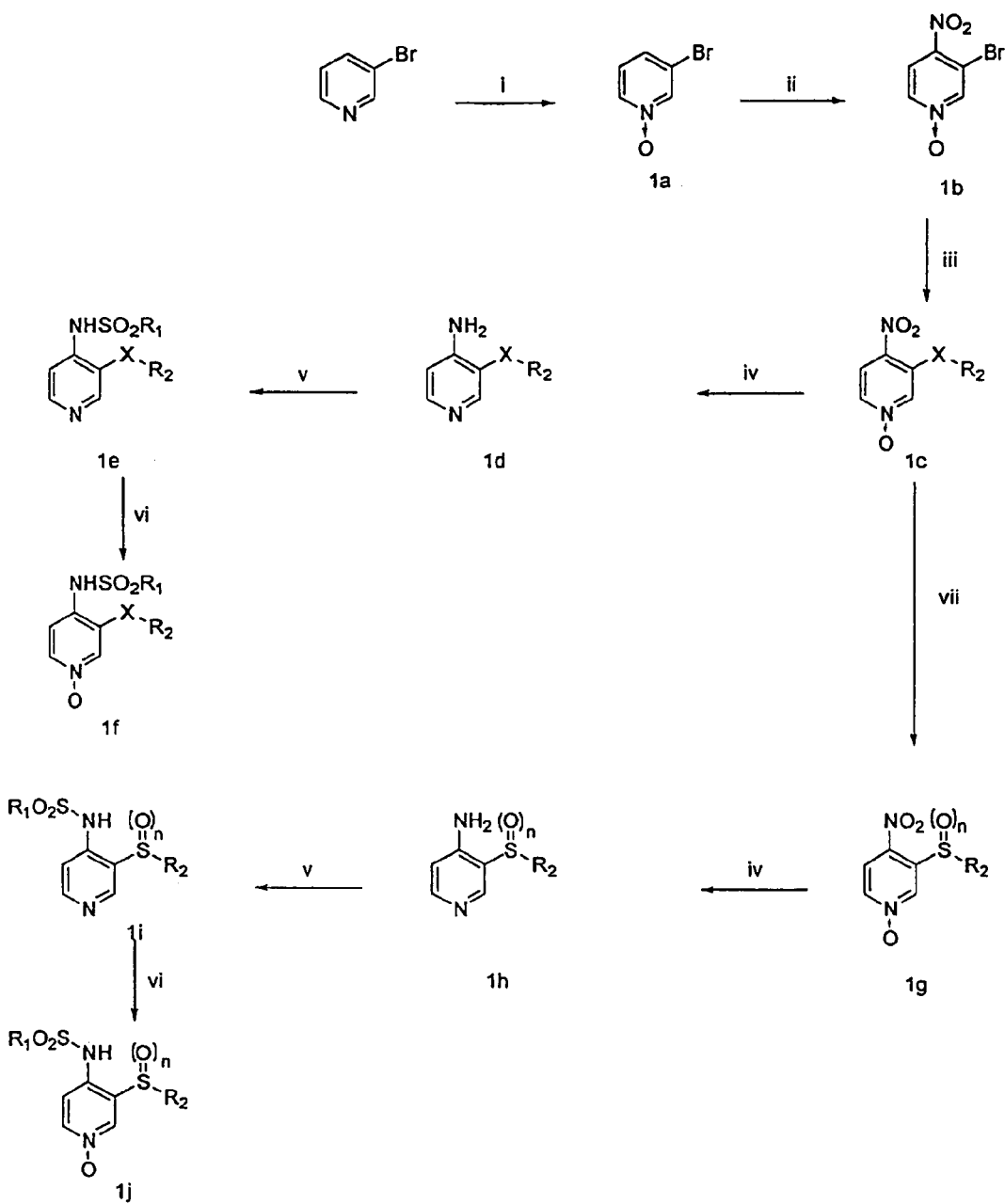

(i) $H_2O_2$ (ii) $HNO_3$ / $H_2SO_4$ (iii) $KMnO_4$ (iv) 1. $SOCl_2$ 2. $NH_3$ 3. deshydratation (v) $R_2MgBr$ (vi) $HOCH_2CH_2OH$ (vii) Fe $CH_3COOH$ (viii) $R_1SO_2Cl$, $K_2CO_3$ (ix) HCl (x) $NH_2-NH_2$, KOH (xi) $H_2O_2$

PYRIDINIC SULFONAMIDE DERIVATIVES METHOD OF PRODUCTION AND USE THEREOF

This is a nationalization of PCT/EP02/10532 filed Sep. 19, 2002 and published in English.

The present invention relates to new pyridinic sulfonamides, to their method of production, to pharmaceutical compositions comprising such derivatives and their use as active therapeutic substance in the treatment of diseases.

The new pyridinic sulfonamide derivatives, according to the invention, are represented by a general formula (I):

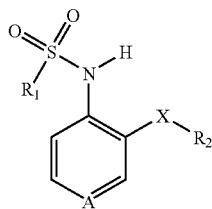

Formula (I)

wherein
- A represents a Nitrogen or a —N═O group;
- X represents Oxygen, Sulphur or an element selected from the group consisting of (—NR$_3$, —CR$_3$R$_4$, —SO, —SO$_2$, or —CO); wherein R$_3$ and R$_4$ which can be identical or different, denotes each independently one element selected from the group consisting of (hydrogen, a mono- or polyhalogenated C$_{1-12}$-alkyl, a mono- or polyhalogenated C$_{3-8}$-cycloalkyl, a C$_{1-12}$-alkyl or a C$_{3-8}$-cycloalkyl);
- R$_1$ represents a mono- or polyhalogenated C$_{1-12}$-alkyl, or a mono- or poly-halogenated C$_{3-8}$-cycloalkyl group;
- R$_2$ represents a C$_{3-8}$-cycloalkyl group or an aryl group substituted or not by one or several elements selected from the group consisting of (halogen, C$_{1-12}$-alkyl, C$_{3-8}$-cycloalkyl, R$_1$, hydroxy, C$_{1-6}$-alkoxy, C$_{1-6}$-alkoxy-C$_{1-6}$-alkyl, nitro, amino, cyano, cyanomethyl, perhalomethyl, C$_{1-6}$-monoalkyl- or dialkylamino, sulfamoyl, C$_{1-6}$-alkylthio, C$_{1-6}$-alkylsulfonyl, C$_{1-6}$-alkylsulfinyl, formyl, C$_{1-6}$-alkylcarbonylamino, R$_5$arylthio, R$_5$arylsulfinyl, R$_5$arylsulfonyl, C$_{1-6}$-alkoxycarbonyl, C$_{1-6}$-alkoxycarbonyl-C$_{1-6}$-alkyl, carbamyl, carbamylmethyl, C$_{1-6}$-monoalkyl- or dialkylaminocarbonyl, C$_{1-6}$-monoalkyl- or dialkylaminothiocarbonyl, ureido, C$_{1-6}$-monoalkyl- or dialkylaminocarbonylamino, thioureido, C$_{1-6}$-monoalkyl- or dialkylaminothiocarbonylamino, C$_{1-6}$-monoalkyl- or dialkylaminosulfonyl, carboxy, carboxy-C$_{1-6}$-alkyl, acyl, R$_5$aryl, R$_5$arylalkyl, R$_5$aryloxy),
- where R$_5$ denotes one or several elements selected from the group consisting of (hydrogen, C$_{1-6}$-alkyl, halogen, hydroxy or C$_{1-6}$-alkoxy).

"C$_{1-6}$-alkyl" as used herein, alone or in combination, refers to a straight or branched, saturated hydrocarbon chain having 1 to 6 carbon atoms such as methyl, propyl, butyl, isopentyl, hexyl, 1-methylbutyl, 1,2-dimethylbutyl, 2-ethylbutyl, 2-methylpentyl, 3-methylpentyl and the like.

"C$_{1-12}$-alkyl" as used herein, alone or in combination, refers to a straight or branched, saturated hydrocarbon chain having 1 to 12 carbon atoms.

"C$_{3-8}$-cycloalkyl" as used herein refers to a radical of a saturated cyclic hydrocarbon chain having 3 to 8 carbon atoms such as cyclopropyl, cyclobutyl, cyclopentyl, cyclohexyl, and the like.

"C$_{1-6}$-alkoxy" as used herein, alone or in combination, refers to a straight or branched monovalent substituent comprising a C$_{1-6}$-alkyl group linked through an ether oxygen having its free valence bond from the ether oxygen and having 1 to 6 carbon atoms such as methoxy, ethoxy, propoxy, isopropoxy, butoxy, pentoxy, tert-butoxy and the like.

"C$_{1-6}$-alkoxy-C$_{1-6}$-alkyl" as used herein refers to a group of 2–12 carbon atoms interrupted by an oxygen atom such as —CH$_2$—O—CH$_3$, —CH$_2$CH$_2$O—CH$_3$, —CH$_2$—O—CH$_2$CH$_3$, —CH$_2$—O—CH(CH$_3$)$_2$, —CH$_2$CH$_2$—O—CH(CH$_3$)$_2$, —CH(CH$_3$)CH$_2$—O—CH$_3$ and the like. CH(CH$_3$)CH$_2$—O—CH$_3$ and the like.

"halogen" means fluorine, chlorine, bromine or iodine.

"perhalomethyl" means trifluoromethyl, trichloromethyl, tribromomethyl or triiodomethyl.

"C$_{1-6}$-monoalkylamino" as used herein refers to an amino group wherein one of the hydrogen atoms is substituted with a straight or branched, saturated hydrocarbon chain having 1 to 6 carbon atoms such as methylamino, ethylamino, propylamino, isopropylamino, butylamino, tert-butylamino, isopentylamino, hexylamino and the like.

"C$_{1-6}$-dialkylamino" as used herein refers to an amino group wherein the two hydrogen atoms independently are substituted with a straight or branched, saturated hydrocarbon chain having 1 to 6 carbon atoms such as dimethylamino, N-ethyl-N-methylamino, N-methyl-N-isopropylamino, N-butyl-N-methylamino, dihexylamino and the like.

"C$_{1-6}$alkylthio" as used herein, alone or in combination, refers to a straight or branched monovalent substituent comprising a C$_{1-6}$-alkyl group linked through a divalent sulfur atom having its free valence bond from the sulfur atom and having 1 to 6 carbon atoms such as methylthio, ethylthio, propylthio, isopropylthio, butylthio, pentylthio, 3-methylpentylthio and the like.

"C$_{1-6}$-alkylsulfonyl" as used herein refers to a monovalent substituent comprising a C$_{1-6}$alkyl group linked through a sulfonyl group (—S(═O)$_2$—) such as methylsulfonyl, ethylsulfonyl, propylsulfonyl, isopropylsulfonyl, butylsulfonyl, pentylsulfonyl, 2-methylpentylsulfonyl and the like.

"C$_{1-6}$-alkylsulfinyl" as used herein refers to a monovalent substituent comprising a C$_{1-6}$-alkyl group linked through a sulfinyl group (—S(═O)—) such as methylsulfinyl, ethylsulfinyl, propylsulfinyl, isopropylsulfinyl, tert-butylsulfinyl, pentylsulfinyl, 2-ethylbutylsulfinyl and the like.

"acyl" as used herein refers to a monovalent substituent comprising a C$_{1-6}$-alkyl group linked through a carbonyl group such as acetyl, propionyl, butyryl, isobutyryl, pivaloyl, valeryl and the like.

"C$_{1-6}$-alkylcarbonylamino" as used herein refers to an amino group wherein one of the hydrogen atoms is substituted with an acyl group such as acetamido, propionamido, iospopropylcarbonylamino 2-ethylbutylcarbonylamino and the like.

"aryl" as used herein refers to phenyl, 1-naphthyl, or 2-naphthyl.

"arylthio" as used herein, alone or in combination, refers to an aryl group linked through a divalent sulfur atom having its free valence bond from the sulfur atom, the aryl group is substituted or not by one or several elements of $R_5$ such as phenylthio, 1-naphthylthio, 2-methylphenylthio, 3-methoxyphenylthio and the like.

"arylsulfinyl" as used herein, alone or in combination, refers to an aryl group linked through a sulfinyl group (—S(=O)—), the aryl group is substituted or not by one or several elements of $R_5$ such as phenylsulfinyl, 2-methylphenylsulfinyl, 3-chloro-1-naphthylsulfinyl and the like.

"arylsulfonyl" as used herein, alone or in combination, refers to an aryl group linked through a sulfonyl group (—S(=O)$_2$—), the aryl group is substituted or not by one or several elements of $R_5$ such as phenylsulfonyl, 2-methylphenylsulfonyl, 4-iodophenylsulfonyl, 2-naphthylsulfonyl and the like.

"$C_{1-6}$-alkoxycarbonyl" as used herein refers to a monovalent substituent comprising a $C_{1-6}$-alkoxy group linked through a carbonyl group such as methoxycarbonyl, isopropoxycarbonyl, butoxycarbonyl, tert-butoxycarbonyl, 2-methylpentoxycarbonyl and the like.

"$C_{1-6}$-monoalkylaminocarbonyl" as used herein refers to a monovalent substituent comprising a $C_{1-6}$-monoalkylamino group linked through a carbonyl group such as methylaminocarbonyl, isopropylaminocarbonyl, butylaminocarbonyl, 2-methylbutylaminocarbonyl and the like.

"$C_{1-6}$-dialkylaminocarbonyl" as used herein refers to a monovalent substituent comprising a $C_{1-6}$-dialkylamino group linked through a carbonyl group such as dimethylaminocarbonyl, diethylaminocarbonyl N-methyl-N-isopropylaminocarbonyl, N-methyl-N-butylaminocarbonyl, N-propyl-N-2-methylbutylaminocarbonyl and the like.

"$C_{1-6}$-monoalkylaminothiocarbonyl" as used herein refers to a monovalent substituent comprising a $C_{1-6}$-monoalkylamino group linked through a thiocarbonyl group such as methylaminothiocarbonyl, isopropylaminothiocarbonyl, butylaminothiocarbonyl, 3-methylpentylaminothiocarbonyl, 1,2-dimethylbutylaminothiocarbonyl and the like.

"$C_{1-6}$-dialkylaminothiocarbonyl" as used herein refers to a monovalent substituent comprising a $C_{1-6}$-dialkylamino group linked through a thiocarbonyl group such as dimethylaminothiocarbonyl, diethylaminothiocarbonyl N-methyl-N-isopropylaminothiocarbonyl, N-methyl-N-butylaminothiocarbonyl N-tert-butyl-N-hexylaminothiocarbonyl and the like.

"$C_{1-6}$-monoalkylaminocarbonylamino" as used herein refers to an amino group wherein one of the hydrogen atoms is substituted with a $C_{1-6}$-monoalkylaminocarbonyl group such as methylaminocarbonylamino, ethylaminocarbonylamino, propylaminocarbonylamino, 3-methylbutylaminocarbonylamino, 1,2-dimethylbutylaminocarbonylamino and the like.

"$C_{1-6}$-dialkylaminocarbonylamino" as used herein refers to an amino group wherein one of the hydrogen atoms is substituted with a $C_{1-6}$-dialkylaminocarbonyl group such as dimethylaminocarbonylamino, diethylaminocarbonylamino, N-methyl-N-ethylaminocarbonylamino, N-methyl-N-isopropylaminocarbonylamino, N-propyl-N-pentylaminocarbonylamino and the like.

"$C_{1-6}$-monoalkylaminothiocarbonylamino" as used herein refers to an amino group wherein one of the hydrogen atoms is substituted with a $C_{1-6}$-monoalkylaminothiocarbonyl group such as methylaminothiocarbonlamino, ethylaminothiocarbonylamino, propylaminothiocarbonylamino, 3-methylpentylaminothiocarbonylamino and the like.

"$C_{1-6}$-dialkylaminothiocarbonylamino" as used herein refers to an amino group wherein one of the hydrogen atoms is substituted with a $C_{1-6}$ dialkylaminothiocarbonyl group such as dimethylaminothiocarbonylamino, diethylaminothiocarbonylamino, N-methyl-N-ethylaminothiocarbonylamino, N-methyl-N-propylaminothiocarbonylamino, N-isopropyl-N-hexylaminothiocarbonylamino, N-3-methylpentyl-N-pentylaminothiocarbonylamino and the like.

"$C_{1-6}$-monoalkylaminosulfonyl" as used herein refers to a monovalent substituent comprising a $C_{1-6}$-monoalkylamino group linked through a sulfonyl group such as methylaminosulfonyl, ethylaminosulfonyl, propylaminosulfonyl, hexylaminosulfonyl, tert-butylaminosulfonyl, 1,2-dimethylbutylaminosulfonyl and the like.

"$C_{1-6}$-dialkylaminosulfonyl" as used herein refers to a monovalent substituent comprising a $C_{1-6}$-dialkylamino group linked through a sulfonyl group such as dimethylaminosulfonyl, diethylaminosulfonyl, N-methyl-N-ethylaminosulfonyl N-methyl-N-propylaminosulfonyl, N-hexyl-N-3-methylbutylaminosulfonyl and the like.

"ureido" as used herein means —NH—CO—NH$_2$.

"thioureido" as used herein means —NH—CS—NH$_2$.

"arylalkyl" as used herein refers to a straight or branched saturated carbon chain containing from 1 to 6 carbons substituted with an aromatic carbohydride the aryl group is substituted or not by one or several elements of $R_5$.

"aryloxy" as used herein refers to phenoxy, 1-naphthyloxy or 2-naphthyloxy, the aryl group is substituted or not by one or several elements of $R_5$.

"$R_5$aryl as used herein refers to aryl substituted or not by $R_5$.

This invention also refers to all optical isomers of pyridinic sulfonamides derivatives covered by the formula (I), particularly the optically active isomers, and their mixtures including racemic mixtures thereof. When in the general formula (I), one has an asymetrical carbon atom, the invention refers as well to pure optical isomers than to racemic mixture.

The invention refers also to tautomeric forms of the pyridinic sulfonamide derivatives and to pharmacologically acceptable salts of the derivatives covered by formula (I).

By pharmacologically acceptable salts of the derivatives, one means pharmaceutically acceptable acid addition salts, pharmaceutically acceptable metal salts or optionally alkylated ammonium salts.

Preferred classes of pyridine sulfonamides derivatives according to the general formula are especially those in which $R_1$ is trifluoromethyl.

The most preferred pyridine sulfonamide is N-(3-phenoxy-4-pyridinyl)trifluoromethanesulfonamide.

In another aspect, the invention also relates to a method of producing the above mentioned derivatives. The method comprises the steps of a) converting into pyridine N-oxide, a pyridinic compound unsubstituted in position 4 and b) reacting the resulted pyridine N-oxide with a nitration reagent to obtain a 4-nitrosubstituted pyridine N-oxide derivative.

The pyridinic compound may be any pyridinic derivative unsubstituted in position 4 and susceptible to react with an oxydant such as $H_2O_2$.

Figure 2:
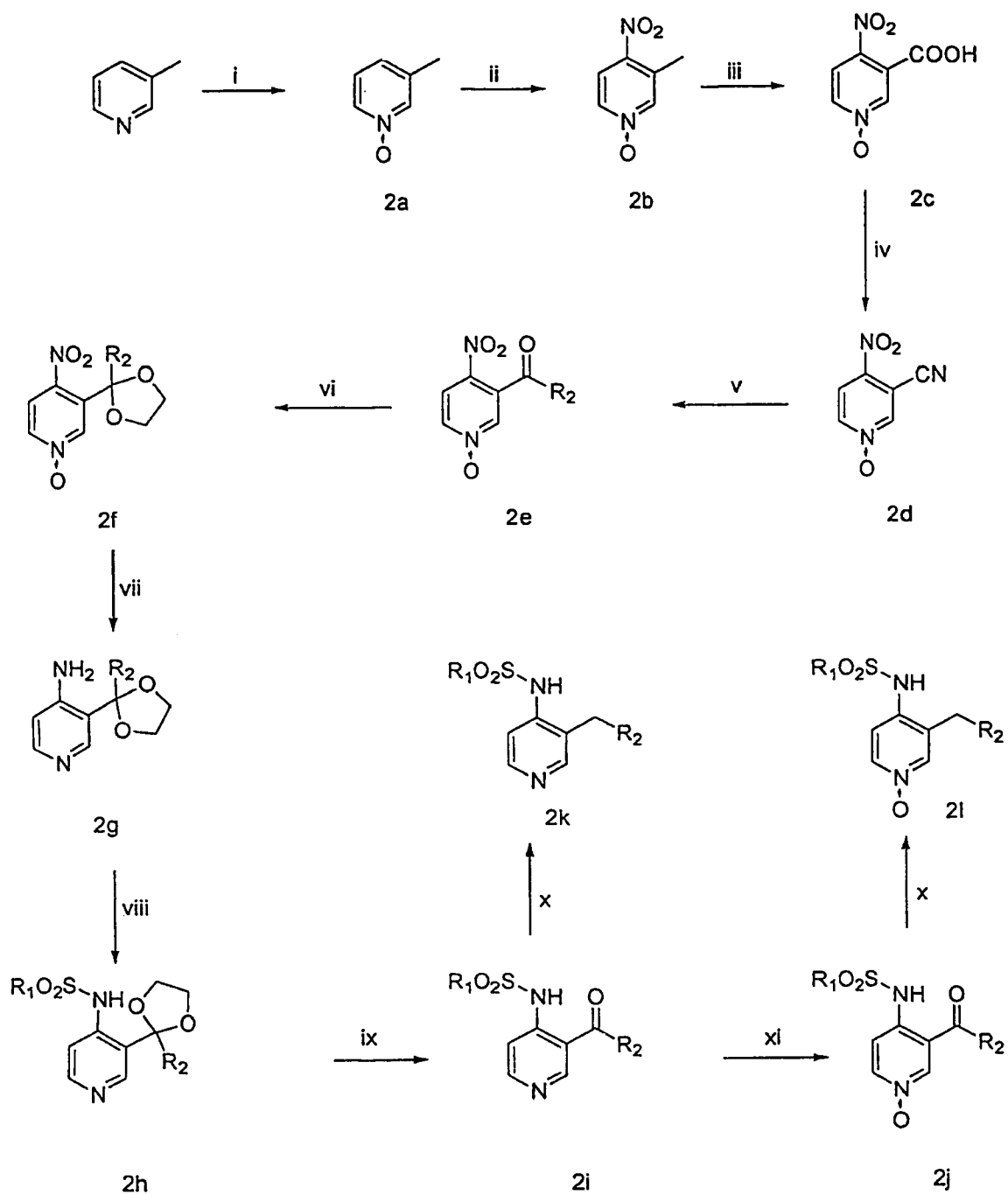

The pyridinic compound unsubstituted in the 4-position may be for example 3-bromopyridine or 3-methylpyridine as illustrated in FIGS. 1 and 2.

Conversion of pyridinic compound into the pyridine N-oxyde is described for example in Organic Syntheses, Coll. Vol, IV, p 828, 1963.

By nitration agent one means a mixture from 1:1 to 1:2 parts of concentrated nitric acid and concentrated sulphuric acid to be added between RT to 100° C. and under continuous stirring to the pyridine N-oxide.

The method of production of the pyridinic sulfonamide derivatives is illustrated in FIGS. 1 and 2 wherein.

FIG. 1 represents a schematic synthesis of compounds with an O, S, SO, $SO_2$, $NR_3$ and $CR_3R_4$ linkage and FIG. 2 represents a schematic synthesis of compounds with a CO and $CH_2$ linkage.

FIG. 1

The pyridine N-oxide of formula 1a may be prepared from 3-bromopyridine which can be oxidized using several oxidants such as $H_2O_2$. The nitration at the 4-position of the pyridine N-oxide can be achieved by a mixture of nitric and sulphuric acids to form 1b. The synthesis of 1c may be realized by reaction of 1b with a cycloalkane derivative such as a cyclopentane, a cyclohexane, a cycloheptane derivative or a benzene derivative in presence of a suitable inorganic base such as $K_2CO_3$ or NaOH in an inert solvent such as acetonitrile or dichloromethane. The nitropyridine N-oxide 1c is converted into the aminopyridine 1d via a reduction reaction using a reductant such as iron in presence of acetic acid. For this reaction, water may be added to the mixture and the temperature may be ranging from room temperature to the reflux of the solvent. The synthesis of the sulfonamide 1e is completed by reaction of the amino-substituted pyridine derivative 1d and the appropriate sulfonyl derivative such as sulfonyl chloride, sulfonyl fluoride or sulfonic anhydride in presence of a suitable inorganic base such as $K_2CO_3$ or NaOH in an inert anhydrous solvent such as acetonitrile, dioxane or dichloromethane. The oxidation of 1e use an oxidant such as $H_2O_2$ to form 1f.

The synthesis of the sulfoxide and the sulfone family 1i and 1j is realized throughout oxidation of the thio derivative 1c by an oxidant such as meta-chloroperbenzoic acid to form 1g. This oxidation is followed by a reduction (1h) and the formation of the sulfonamide (1i) and finally by an oxidation (1j) of the pyridine comparable to the methods used for the preparation of 1d, 1e and 1f.

FIG. 2:

The synthesis of the ceto derivatives is achieved by the pathway of scheme 2. This scheme begins by an oxidation of 3-methylpyridine by hydrogen peroxide in presence of acetic acid (2a). Nitration by nitric acid and sulphuric acid at the 4-position of the N-oxide lead to the formation of 2b. The methyl group of 2b is oxidized by $KMnO_4$ to produce the carboxylic acid 2c. The synthesis of the cyano derivative 2d is achieved in three steps. The first one is a conversion of carboxylic acid into carboxylic halide by $SOCl_2$. The second is the formation of carboxamide and the last step is a deshydration of the amide to form the nitrile 2d. The ceto linkage is prepared by reaction between 2d and an organosmagnesium compound such as an alkyl magnesium bromide or an aryl magnesium bromide. The ceto group is then protected as an acetal by reaction of 2e and ethyleneglycol in an acidic medium. After that, the nitro group and the N-oxide of 2f is reduced by iron in presence of acetic acid to produce 2g. This compound reacts with the appropriate sulfonyl chloride such as an alkyl or an aryl sulfonyl chloride to form the sulfonamide 2h. The acetal may be hydrolysed to generate the ceto compound 2i. The last step is an oxidation of the pyridine 2i by $H_2O_2$ to form 2j. Conversion of the ceto compounds into the corresponding methylene derivatives is achieved by a Wolff-Kishner reaction as described in Organic Reactions, Vol IV, p 378, 1948.

The method of production is also illustrated by examples hereafter.

Elemental analyses (C,H,N,S) have been realised and correspond to the theoretical formula (+/−0.4%). IR and $^1$H-NMR spectra are in accordance with proposed formulas.

The Infra-red spectra (IR) made on 1 mg of different substances have been recorded by means of a FT-IR Perkin Elmer 1750 and KBr pellets of 250 mg.

After dissolution in DMSO-$d_6$, the $^1$H-NMR spectrum of different molecules has been recorded on a Bruker 400 apparatus.

Melting points of obtained molecules have been determined on a Büchi-Tottoli apparatus.

EXAMPLE 1

Preparation of N-(3-phenoxy-4-pyridinyl)trifluoromethane-sulfonamide (Compound I)

Step 1: To 1.58 g of 3-bromopyridine (10 mmol) dissolved in 6 mL of glacial acetic acid, 4 mL of 30% hydrogen peroxide are added. The solution is heated with reflux for 48 hours. The solvent is evaporated under depression. The residue is purified by column chromatography using ethyl acetate as eluent.

Yield: 64% (oil).

IR (KBr): 3109 (C—H), 1595 (C=N), 1468 (C=C), 1292 (N—O) cm$^{-1}$

Step 2: To 1.74 g of 3-bromopyridine N-oxide dissolved in 4 mL of concentrated sulphuric acid, a mixture of 4 mL of concentrated sulphuric acid and 6.7 mL of concentrated nitric acid is added under continuous stirring. The solution is heated at 90° C. for 90 minutes. Then the solution is poured into ice and supplemented with a 50% aqueous solution of NaOH until complete precipitation of the final compound. The yellow solid is filtered off and washed with water to give 1.51 g of 3-bromo-4-nitropyridine N-oxide.

Yield: 69%. mp: 149° C. IR (KBr): 3099 (C—H), 1589 (C=N), 1552, 1338 (NO$_2$), 1295 (N—O), 643 (C—Br) cm$^{-1}$ Step 3: 4.8 mL of 10% aqueous solution of NaOH are added to 1.12 g of phenol. After stirring for 5 minutes, water is evaporated under reduced pressure. A white solid is obtained and taken up by 10 mL of acetonitrile and the resulting suspension is supplemented with 2.19 g of 3-bromo-4-nitropyridine N-oxide. The obtained mixture is heated under reflux during 5 minutes. The mixture is further poured into ice and extracted with ethyl acetate. Organic layers are collected and dried over anhydrous magnesium sulphate. After evaporation of the solvent, a solid residue is purified by column chromatography using ethyl acetate as eluent to give 1.27 g of a yellow solid.

Yield: 54%. mp: 109° C. IR (KBr): 3109 (C—H), 1606 (C=N), 1507, 1313 (NO$_2$), 1219 (N—O)cm$^{-1}$ Step 4: 2.32 g of 4-nitro-3-phenoxypyridine N-oxide dissolved in 55 mL of acetic acid and 14 mL of water are heated under reflux. Then 3.48 g of iron powder are added and the reflux is maintained for 12 hours. The solution is filtered and evaporated under reduced pressure. An oily residue is taken up with water and pH adjusted to 10 by addition of a 10% aqueous solution of NaOH. The suspension is filtered and the filtrate is extracted by ethyl acetate. Organic layers are collected and dried over anhydrous magnesium sulfate. After evaporation, 4-amino-3-phenoxypyridine is obtained as a yellow oil.
Yield: 80–90%.

Step 5: To 1.81 g of 4-amino-3-phenoxypyridine dissolved in 112 mL of dry acetonitrile are added 8.29 g anhydrous potassium carbonate. The suspension is stirred for 5 minutes and 2.02 mL of trifluoromethanesulfonyl chloride are added. The mixture is stirred for 12 h, then filtered and the solvent evaporated under reduced pressure. The residue is taken up with 10% aqueous solution of NaOH and the pH of the solution is adjusted to 5 with 1N HCl to separate 2.53 g of a final compound as a white solid.

Yield: 80%; mp: 239° C.; IR (KBr): 2807, 2728, 2648 ($N^+$—H), 1633 (C=N), 1473 (C=C), 1343, 1129 ($SO_2$) cm$^{-1}$; NMR $^1$H (DMSO-$d_6$): δ6.95 (d, 2H, H-2'+H-6'), 7.11 (t, 1H, H4'), 7.36 (t, 2H, H-3'+H-5'), 7.81 (d, 1H, H-5), 8.30 (d, 1H, H-6), 8.43 (s, 1H, H-2), 13.90 (bs, N—H); Anal ($C_{12}H_9N_2O_3SF_3$) C, H, N, S.

EXAMPLE 2

Preparation of N-(3-(4-chlorophenoxy)-4-pyridinyl)trifluoromethanesulfonamide

Step 1 and step 2: similar to example 1
Step 3: 4 mL of a 10% aqueous solution of NaOH are added to 1.4 g of 4-chlorophenol. After stirring for 5 minutes, water is evaporated under reduced pressure. A white solid is obtained and taken up by 10 mL of acetonitrile and the resulting suspension is supplemented with 2 g of 3-bromo-4-nitropyridine N-oxide to obtain a mixture which is then heated under reflux for 5 minutes. The mixture is further filtered and the filtrate is concentrated under reduced pressure. A solid is obtained and is dissolved in a minimum of methanol and 4-nitro-3-(4-chlorophenoxy)-pyridine N-oxide is precipitated by addition of water. The precipitate is collected by filtration to give 1.15 g of a yellow solid.

Yield: 47%. mp: 101–102° C. IR (KBr): 3117, 3029 (C—H), 1610 (C=N), 1213 (N—O), 1100 cm$^{-1}$ Step 4: 0.37 g of 4-nitro-3-(4-chlorophenoxy)-pyridine N-oxide dissolved in 9 mL of acetic acid and 2 mL of water are heated under reflux. To such warm solution are added 0.5 g of iron powder and the reflux is maintained for 1 hour. A suspension is obtained and filtered and the filtrate is evaporated under reduced pressure. An oily residue is obtained and taken up with water and pH adjusted to 10 by addition of a 10% aqueous solution of NaOH. The resulting suspension is filtered and the filtrate is extracted by ethyl acetate. Organic layers are collected and dried over anhydrous magnesium sulfate. After evaporation, 4-amino-3-(4-chlorophenoxy)pyridine is obtained as a yellow oil.
Yield: 80–90%.

Step 5: To 0.56 g of 4-amino-3-(4-chlorophenoxy)pyridine dissolved in 20 mL of dry acetonitrile is added 1 g of anhydrous potassium carbonate. The suspension is stirred for 5 minutes and 0.794 mL of trifluoromethanesulfonyl chloride are added. The mixture is stirred for 15 minutes, then filtered and the filtrate concentrated under reduced pressure. The residue is taken up with a 10% aqueous solution of NaOH and the pH of the solution is adjusted to 7 with 1N HCl to separate 0.61 g of the final compound as a white solid which is filtered, washed with water and dried.

Yield: 68%; mp: 222–223° C.; IR (KBr): 2810, 2732, 2648 ($N^+$—H), 1636 (C=N), 1474 (C=C), 1344, 1130 ($SO_2$) cm$^{-1}$.

EXAMPLE 3

Preparation of N-(3-(3,5-dichlorophenoxy)-4-pyridinyl)trifluoromethanesulfonamide Step 1 and tep 2: similar to example 1
Step 3: 4.32 mL of a 10% aqueous solution of NaOH are added to 1.76 g of 3,5-dichlorophenol. After stirring for 5 minutes, water is evaporated under reduced pressure. A white solid is obtained and taken up by 10 mL of acetonitrile and the suspension is supplemented with 2 g of 3-bromo-4-nitropyridine N-oxide and then heated under reflux for 20 hours. The mixture is filtered and the filtrate is concentrated under reduced pressure. A solid is obtained and is suspended in a minimum of cold methanol and 4-nitro-3-(3,5-dichlorophenoxy)pyridine N-oxide is collected by filtration to give 1.25 g of a yellow final solid.

Yield: 47%. mp: 160–161° C. IR (KBr): 3051, 3014 (C—H), 1610 (C=N), 1584, 1309 ($NO_2$), 1227 (N—O) cm$^{-1}$ Step 4: 0.95 g of 4-nitro-3-(3,5-dichlorophenoxy)pyridine N-oxide dissolved in 18 mL of acetic acid and 5 mL of water are heated under reflux. To the warm solution are added 1.12 g of iron powder and the reflux is maintained for 12 hours. The solution is filtered and the filtrate is evaporated under reduced pressure. An oily residue is obtained and taken up with water and the pH adjusted to 10 by addition of a 10% aqueous solution of NaOH. The suspension is filtered and the filtrate is extracted by ethyl acetate. Organic layers are collected and dried over anhydrous magnesium sulfate. After evaporation, 4-amino-3-(3,5-dichlorophenoxy)pyridine is obtained as a yellow oil.
Yield: 80–90%.

Step 5: To 0.45 g of 4-amino-3-(3,5-dichlorophenoxy)pyridine dissolved in 20 mL of dry acetonitrile are added 0.73 g anhydrous potassium carbonate. The suspension is stirred for 5 minutes and 0.551 mL of trifluoromethanesulfonyl chloride are added. The mixture is stirred for 30 minutes, then filtered and the filtrate concentrated under reduced pressure. A residue is obtained and taken up with a 10% aqueous solution of NaOH and the pH of the solution is adjusted to 7 with 1N HCl to separate 0.33 g of the final compound as a white solid which is filtered, washed with water and dried.

Yield: 49%; mp: 219–220° C.; IR (KBr): 2921, 2820, 2653 ($N^{+-H}$) 1633 (C=N), 1486 (C—C), 1344, 1126 ($SO_2$) cm$^{-1}$.

EXAMPLE 4

Preparation of N-(3-(4-bromophenoxy)-4-pyridinyl)trifluoromethanesulfonamide

Step 1 and step 2: similar to example 1
Step 3: 5.5 mL of a 10% aqueous solution of NaOH are added to 1.88 g of 4-bromophenol. After stirring for 5 minutes, water is evaporated under reduced pressure. A white solid is obtained and taken up by 10 mL of acetonitrile and the suspension is supplemented with 2 g of 3-bromo-4-nitropyridine N-oxide and then heated under reflux 5 minutes. The mixture is filtered and the filtrate is evaporated under reduced pressure. A solid is obtained and is dissolved in a minimum of methanol and 4-nitro-3-(4-bromophenoxy)-pyridine N-oxide is precipitated by addition of water. The precipitated is collected by filtration, washed with water and dried, to give 0.96 g of a yellow solid.

Yield: 34%. mp: 124–125° C. IR (KBr): 3106 (C—H), 1605 (C=N), 1565, 1312 (NO$_2$), 1212 (N—O)cm$^{-1}$ Step 4: 3 g of 4-nitro-3-(4-bromophenoxy)-pyridine N-oxide dissolved in 72 mL of acetic acid and 18 mL of water are heated under reflux. To the warm solution are added 4.2 g of iron powder and the reflux is maintained for 12 hours. The solution is filtered and the filtrate is evaporated under reduced pressure. Oily residue is obtained and is taken up with water and the pH adjusted to 10 by addition of a 10% aqueous solution of NaOH. The suspension is filtered and the filtrate is extracted by ethyl acetate. Organic layers are collected and dried over anhydrous magnesium sulfate. After evaporation, 4-amino-3-(4-bromophenoxy)-pyridine is obtained as a yellow oil.

Yield: 80–90%.

Step 5: To 0.2 g of 4-amino-3-(4-bromophenoxy)-pyridine dissolved in 20 mL of dry acetonitrile are added 2.25 g anhydrous potassium carbonate.

The suspension is stirred for 5 minutes and 0.235 mL of trifluoromethanesulfonyl chloride are added. The mixture is stirred for 1 hour, then filtered and the filtrate concentrated under reduced pressure. A residue is taken up with a 10% aqueous solution of NaOH and the pH of the solution is adjusted to 7 with 1N HCl to separate 0.21 g of the final compound as a white solid.

Yield: 70%; mp: 245–246° C.; IR (KBr): 2809, 2732, 2648 (N$^+$—H), 1635 (C=N), 1473 (C=C), 1344, 1130 (SO$_2$) cm$^{-1}$.

EXAMPLE 5

Preparation of N-(3-(3-chlorophenoxy)-4-pyridinyl)trifluoromethanesulfonamide

Step 1 and step 2: similar to example 1

Step 3: 4 mL of a 10% aqueous solution of NaOH are added to 1.4 g of 3-chlorophenol. After stirring for 5 minutes, water is evaporated under reduced pressure. A white solid is obtained and taken up by 40 mL of acetonitrile and the suspension is supplemented with 2 g of 3-bromo-3-nitropyridine N-oxide and then heated under reflux for 5 minutes. The mixture is filtered and the filtrate is concentrated under reduced pressure. A solid is obtained and is dissolved in a minimum of cold methanol and 4-nitro-3-(3-chlorophenoxy)-pyridine N-oxide is collected by filtration to give 1.06 g of a yellow solid.

Yield: 42%. mp: 105–106° C. IR (KBr): 3056 (C—H), 1604 (C=N), 1568, 1318 (NO$_2$), 1219 (N—O)cm$^{-1}$ Step 4: 1 g of 4-nitro-3-(3-chlorophenoxy)-pyridine N-oxide dissolved in 20 mL of acetic acid and 6 mL of water are heated under reflux. To the warm solution are added 2.98 g of iron powder and then heated under reflux for 3 hours. The suspension is filtered and the filtrate is concentrated under reduced pressure. Oily residue is obtained and taken up with water and the pH adjusted to 10 by addition of a 10% aqueous solution of NaOH. The suspension is filtered and the filtrate is extracted by ethyl acetate. Organic layers are collected and dried over anhydrous magnesium sulfate. After evaporation, 4-amino-3-(3-chlorophenoxy)pyridine is obtained as a yellow oil.

Yield: 90%.

Step 5: To 0.2 g of 4-amino-3-(3-chlorophenoxy)pyridine dissolved in 15 mL of dry dichloromethane are added 0.5 mL of triethylamine. The solution is stirred for 5 minutes and 0.19 mL of trifluoromethanesulfonyl chloride are added. The mixture is stirred for 12 h, then filtered and the filtrate concentrated under reduced pressure. The residue is taken up with a 10% aqueous solution of NaOH and the pH of the solution is adjusted to 7 with 1N HCl to separate 0.2 g of the final compound as a white solid which is filtered, washed with water and dried.

Yield: 73%; mp: 198–199° C.; IR (KBr): 2896, 2815, 2650 (N$^+$—H), 1632 (C=N), 1473 (C=C), 1343, 1129 (SO$_2$) cm$^{-1}$.

EXAMPLE 6

Preparation of N-(3-thiophenoxy-4-pyridinyl)trifluoromethanesulfonamide

Step 1 and step 2: similar to example 1

Step 3: 2 mL of thiophenol is dissolved in 80 mL of toluene. 2.5 g of K$_2$CO$_3$ is added and the suspension is heated until reflux occur. Then, 4 g of 3-bromo-4-nitropyridine N-oxide is added and the reflux is maintained for 2 hours. The mixture is filtered and the filtrate is concentrated under reduced pressure. A residue is taken up by a minimum of cold ethanol and 4-nitro-3-thiophenoxypyridine N-oxide is collected by filtration to give 2.52 g of a yellow solid.

Yield: 55%. mp: 147–148° C. IR (KBr): 3065 (C—H), 1588 (C=N), 1548, 1329 (NO$_2$), 1230 (N—O)cm$^{-1}$ Step 4: 0.5 g of 4-nitro-3-thiophenoxypyridine N-oxide dissolved in 20 mL of glacial acetic acid are heated under reflux. To the warm solution are added 0.37 g of iron powder and the reflux is maintained for 2 hours. The solution is filtered and the filtrate concentrated under reduced pressure. Oily residue is obtained and taken up with water and the pH adjusted to 10 by addition of a 10% aqueous solution of NaOH solution. The suspension is filtered and the filtrate is extracted by ethyl acetate. Organic layers are collected and dried over anhydrous magnesium sulfate. After evaporation, 4-amino-3-thiophenoxypyridine is obtained as a yellow oil.

Yield: 90%.

Step 5: To 0.45 g of 4-amino-3-thiophenoxypyridine dissolved in 20 mL of dry acetonitrile are added 1.84 g anhydrous potassium carbonate. The suspension is stirred for 5 minutes and 0.47 mL of trifluoromethanesulfonyl chloride are added. The mixture is stirred for 4 h, then filtered and acetonitrile is evaporated under reduced pressure. The residue is taken up with a 10% aqueous solution of NaOH and the pH of the solution is adjusted to 5 with 1N HCl to separate 0.36 g of the final compound as a white solid which is filtered, washed with water and dried.

Yield: 50%; mp: 188–189° C.; IR (KBr): 2807, 2728, 2648 (N$^+$—H), 1633 (C=N), 1473 (C=C), 1343, 1129 (SO$_2$ The invention also refers to the use of the pyridinic sulfonamides derivatives covered by formula (1) and their salts for drug manufacture for treatment and/or prevention of diseases such as inflammation, arthrosis, cancer, angiogenesis and asthma and for other pathologies in which they can play a role of COX-2 selective inhibitor.

Prostaglandins (PG) are key mediators involved in the inflammation processes. According to Bergström, S.; Ryhage, R.; Samuelsson, B.; Sjövall, J. in *J. Bio. Chem.*, 1963, 238, 3555–3563, prostaglandins are synthesized by cyclooxygenases (COXs) from arachidonic acid.

Different classes of anti-inflammatory drugs on the market inhibit the synthesis of PG by inhibiting those enzymes.

The COX enzymes exist under two distinct isoforms. COX-1 is a constitutive enzyme responsible for physiological production of PG. This enzyme is involved in several homeostatic processes and is thus considered as a "house keeping" enzyme. In contrast, COX-2 is an inducible enzyme which is mainly produced during inflammation processes. Furthermore, according to Crofford L., Lipsky P., Brooks P., Abramson S., Simon L., van de Putte L. in. *Arthritis Rheum.*, 2000, 43, 4–13, COX-2 is expressed during different pathologies such as arthrosis, angiogenesis and asthma.

A problem with the inhibition of COX-1 by common non-steroidal anti-inflammatory drugs (NSAID) is its side effects such as gastric ulceration.

The present invention deals with the use of new COX-2 selective inhibitors represented by the pyridinic sulfonamide derivatives described above. Such new COX-2 selective inhibitors advantageously does not exhibit such side effects.

The pyridinic sulfonamide derivatives described above have been evaluated as COX inhibitors on one in vitro test and on one in vivo test. For the in vitro assay the methodology is described by X. de Leval, J. Delarge, P. Devel, P. Neven, C. Michaux, B. Masereel, B. Pirotte, J.-L. David, Y. Henrotin, J.-M. Dogné. in *Prostaglandins, Leukot., Essent. Fatty Acids*, 2001, 64, 211–216.

Pharmacological evaluations of N-(3-phenoxy-4-pyridinyl)trifluoro-methanesulfonamide (compound 1) are recorded in Table 1 which describes Estimated $IC_{50}$ for compound 1 on whole blood assay

| compound | $IC_{50}$ COX-1 ($\mu M$) | $IC_{50}$ COX-2 ($\mu M$) | $IC_{50}$ COX-1/ $IC_{50}$ COX-2 |
|---|---|---|---|
| 1 | 2.2 | 0.4 | 5.28 |

The activity of the derivatives has also been evaluated by using a rat paw oedema pharmacological model.

In Carrageenin-induced rat paw oedema model, Wistar rats were used. The mean weight of the animals was 250 g. The animals were treated with an intraperitoneal injection of the drug at the appropriate concentration (solution at the concentration of 10 mg/mL in DMSO). Lambda carrageenin (0.1 mL; 1%) was injected one hour later in the plantar region of the right hand paw. Three hours thereafter, the rats were euthanasied by injection of nembutal (100 mg/kg) and the paws were cutted at the ankle. The swelling was calculated as a percentage increase in the weight of the control paw.

Table 2 reports the effect of compound 1 on rat paw oedema

| compound | 5 (mg/kg) | 10 (mg/kg) | 30 (mg/kg) | Control |
|---|---|---|---|---|
| 1 | 101.0 ± 8.1 | 74.7 ± 7.2 | 54.1 ± 17.5 | 96 ± 8.7 |

Results are expressed as percentage of growth of the paw after injection of carrageneen (mean±standard deviation, n=6).

Those tables clearly show that compound 1 is active as COX-2 inhibitor and presents an anti-inflammatory effect in vivo.

The invention also refers to a Pharmaceutical composition comprising a pyridinic sulfonamide derivative or a pharmaceutical acceptable salt thereof with a pharmaceutical acceptable acid or base, or any optical isomer or mixture of optical isomers, including a racemic mixture or any tautomeric form together with one or more acceptable carriers or diluents.

The pharmaceutical composition may be in a form of an oral dosage unit or parenteral dosage unit.

What is claimed is:

1. A pyridinic sulfonamide derivative represented by a formula (I):

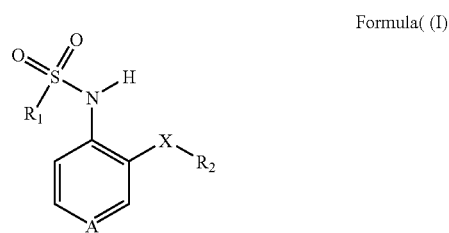

Formula (I)

wherein

A represents a Nitrogen or a —N═O group;

X represents Oxygen, Sulphur or an element selected from the group consisting of —$NR_3$, —$CR_3R_4$, —SO, —$SO_2$, and —CO; wherein $R_3$ and $R_4$ which can be identical or different, denotes each independently one element selected from the group consisting of hydrogen, a mono- or polyhalogenated $C_{1-12}$-alkyl, a mono- or polyhalogenated $C_{3-8}$-cycloalkyl, a $C_{1-12}$-alkyl and a $C_{3-8}$-cycloalkyl;

$R_1$ represents a mono- or polyhalogenated $C_{1-12}$-alkyl or a mono or poly-halogenated $C_{3-8}$-cycloalkyl group;

$R_2$ represents a $C_{3-8}$-cycloalkyl group or a non-substituted aryl group or an aryl group wherein one or more of hydrogen atom(s) of the aryl group is/are substituted by one of the elements selected from the group consisting of halogen, $C_{1-12}$-alkyl, $C_{3-8}$-cycloalkyl, $R_1$, hydroxy, $C_{1-6}$-alkoxy, $C_{1-6}$-alkoxy-$C_{1-6}$-alkyl, nitro, amino, cyano, cyanomethyl; perhalomethyl, $C_{1-6}$-monoalkyl- or dialkylamino, sulfamoyl, $C_{1-6}$-alkylthio, $C_{1-6}$-alkylsulfonyl, $C_{1-6}$-alkylsulfinyl, formyl, $C_{1-6}$-alkylcarbonylamino, $R_5$-arylthio, $R_5$-arylsulfinyl, $R_5$-arylsulfonyl, $C_{1-6}$-alkoxycarbonyl, $C_{1-6}$-alkoxycarbonyl-$C_{1-6}$-alkyl; carbamyl; carbamylmethyl; $C_{1-6}$-monoalkyl- or dialkylaminocarbonyl, $C_{1-6}$-monoalkyl- or dialkylaminothiocarbonyl, ureido, $C_{1-6}$-monoalkyl- or dialkylaminocarbonylamino, thioureido, $C_{1-6}$-monoalkyl- or dialkylaminothiocarbonylamino, $C_{1-6}$-monoalkyl- or dialkylaminosulfonyl, carboxy, carboxy-$C_{1-6}$-alkyl, acyl, $R_5$-aryl, $R_5$-arylalkyl, and $R_5$-aryloxy, where $R_5$ denotes one or several elements selected from the group consisting of hydrogen, $C_{1-6}$-alkyl, halogen, hydroxy and $C_{1-6}$-alkoxy.

2. The pyridinic sulfonamide derivative according to claim 1 characterised in that $R_1$ is trifluoromethyl.

3. The pyridinic sulfonamide derivative according to claim 2 characterised in that A is Nitrogen, X is oxygen, $R_1$ is trifluoromethyl and $R_2$ is phenyl.

4. A method of producing a pyridinic sulfonamide derivative comprising the steps of a) providing, a pyridinic compound unsubstituted in position 4; and b) reacting the pyridinic compound with an oxidant to obtain a corresponding pyridine N-oxide;

c) reacting the resulted pyridine N-oxide with a nitration reagent to obtain a 4-nitrosubstituted pyridine N-oxide derivative;

d) obtaining a 4-amino-pyridine derivative from the 4-nitrosubstituted pyridine N-oxide derivative through a reduction reaction;

e) reacting the 4-amino-pyridine derivative with a sulfonyl derivative to obtain a pyridinic sulphonamide derivative as represented by a formula (I):

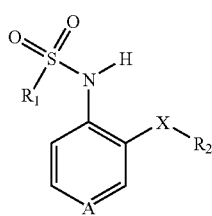

Formula (I)

wherein

A represents a Nitrogen or a —N═O group;

X represents Oxygen, Sulphur or an element selected from the group consisting of —NR$_3$, —CR$_3$R$_4$, —SO, —SO$_2$, and —CO—; wherein R$_3$ and R$_4$ which can be identical or different, denotes each independently one element selected from the group consisting of hydrogen, a mono- or polyhalogenated C$_{1-12}$-alkyl, a mono- or polyhalogenated C$_{3-8}$-cycloalkyl, a C$_{1-12}$-alkyl and a C$_{3-8}$-cycloalkyl;

R$_1$ represents a mono- or polyhalogenated C$_{1-12}$-alkyl or a mono or poly-halogenated C$_{3-8}$-cycloalkyl group;

R$_2$ represents a C$_{3-8}$-cycloalkyl group or a non-substituted aryl group or an aryl group wherein one or more of hydrogen atom(s) of the aryl group is/are substituted by one of the elements selected from the group consisting of halogen, C$_{1-12}$-alkyl, C$_{3-8}$-cycloalkyl, R$_1$, hydroxy, C$_{1-6}$-alkoxy, C$_{1-6}$-alkoxy-C$_{1-6}$-alkyl, nitro, amino, cyano, cyanomethyl; perhalomethyl, C$_{1-6}$-monoalkyl- or dialkylamino, sulfamoyl, C$_{1-6}$-alkylthio, C$_{1-6}$-alkylsulfonyl, C$_{1-6}$-alkylsulfinyl, formyl, C$_{1-6}$-alkylcarbonylamino, R$_5$-arylthio, R$_5$-arylsulfinyl, R$_5$-arylsulfonyl, C$_{1-6}$-alkoxycarbonyl, C$_{1-6}$-alkoxycarbonyl-C$_{1-6}$-alkyl; carbamyl; carbamylmethyl; C$_{1-6}$-monoalkyl- or dialkylaminocarbonyl, C$_{1-6}$-monoalkyl- or dialkylaminothiocarbonyl, ureido, C$_{1-6}$-monoalkyl- or dialkylaminocarbonylamino, thioureido, C$_{1-6}$-monoalkyl- or dialkylaminothiocarbonylamino, C$_{1-6}$-monoalkyl- or dialkylaminosulfonyl, carboxy, carboxy-C$_{1-6}$-alkyl, acyl, R$_5$-aryl, R$_5$-arylalkyl, R$_5$-aryloxy, where R$_5$ denotes one or several elements selected from the group consisting of hydrogen, C$_{1-6}$-alkyl, halogen, hydroxy and C$_{1-6}$-alkoxy.

5. A method of treating inflammation comprising the step of administering a pharmaceutically effective amount of pyridinic sulfonamide derivative according to claim 1, or a pharmaceutically acceptable salt thereof with a pharmaceutically acceptable acid or base or an optical isomer or a mixture of optical isomers, or a tautomeric form.

6. A pharmaceutical composition comprising a pharmaceutically effective amount of pyridinic sulfonamide derivative according to claim 1 or a pharmaceutical acceptable salt thereof with a pharmaceutical acceptable acid or base, or any optical isomer or a mixture of optical isomers, or tautomeric form together with one or more acceptable carriers or diluents.

7. The pharmaceutical composition according to claim 6 in a form of an oral dosage unit or parenteral dosage unit.

8. A method of treating inflammation comprising administering an effective amount of the pharmaceutical composition according to claim 6.

* * * * *